United States Patent
Sykes

(10) Patent No.: US 7,997,147 B2
(45) Date of Patent: Aug. 16, 2011

(54) SHEAR TEST DEVICE

(75) Inventor: Robert John Sykes, Essex (GB)

(73) Assignee: Nordson Corporation, Westlake, OH (US)

( * ) Notice: Subject to any disclaimer, the term of this patent is extended or adjusted under 35 U.S.C. 154(b) by 0 days.

(21) Appl. No.: 12/764,191

(22) Filed: Apr. 21, 2010

(65) Prior Publication Data

US 2010/0218616 A1    Sep. 2, 2010

Related U.S. Application Data

(63) Continuation of application No. 11/573,005, filed as application No. PCT/GB2005/003105 on Aug. 5, 2005, now Pat. No. 7,730,790.

(30) Foreign Application Priority Data

Aug. 10, 2004  (GB) .................................. 0417773.9
Jul. 6, 2005    (GB) .................................. 0513896.1

(51) Int. Cl.
    *G01N 3/24*  (2006.01)
(52) U.S. Cl. .......................... 73/842; 73/150 A; 73/760
(58) Field of Classification Search ............ 73/760–842, 73/150 A
    See application file for complete search history.

(56) References Cited

U.S. PATENT DOCUMENTS

| | | | |
|---|---|---|---|
| 3,662,312 A | 5/1972 | Thorp et al. | |
| 3,805,601 A | 4/1974 | Jeffers | |
| 3,821,785 A | 6/1974 | Rose | |
| 4,709,383 A * | 11/1987 | Goto et al. | 378/72 |
| 4,953,973 A * | 9/1990 | Leftheris et al. | 356/32 |
| 5,166,910 A | 11/1992 | Batzle et al. | |
| 5,178,005 A | 1/1993 | Peterson | |
| 5,255,562 A | 10/1993 | Yamamoto et al. | |
| 5,938,503 A | 8/1999 | Cook et al. | |
| 6,078,387 A | 6/2000 | Sykes | |
| 6,178,823 B1 | 1/2001 | Sykes | |
| 6,237,422 B1 | 5/2001 | Sykes | |
| 6,301,971 B1 | 10/2001 | Sykes | |
| 6,532,825 B1 * | 3/2003 | Abe | 73/804 |
| 6,964,202 B2 * | 11/2005 | Buttle et al. | 73/799 |
| 7,387,030 B1 * | 6/2008 | deLaneuville | 73/808 |
| 7,555,961 B2 | 7/2009 | Sykes | |
| 7,730,790 B2 * | 6/2010 | Sykes | 73/842 |
| 2008/0314159 A1 | 12/2008 | Sykes | |

(Continued)

FOREIGN PATENT DOCUMENTS

GB    1094862    12/1967

(Continued)

OTHER PUBLICATIONS

European Patent Office, Office Action issued in related European Application No. 05 769 271.7 dated Oct. 4, 2010.
The International Bureau of WIPO, International Preliminary Report on Patentability issued in related International Application No. PCT/GB2005/003105 dated Feb. 22, 2007.

(Continued)

*Primary Examiner* — Max Noori
(74) *Attorney, Agent, or Firm* — Wood, Herron & Evans, LLP

(57) ABSTRACT

Shear test apparatus for gold and solder balls of a semiconductor substrate comprises a support element (21) on which is provided a piezo-electric crystal (24) in the direct shear load path. The crystal (24) may have a shield (25). The interface between shield and crystal, and crystal and support element may include an epoxy resin layer to distribute force and retain the components as a unit.

5 Claims, 5 Drawing Sheets

U.S. PATENT DOCUMENTS

2010/0116063 A1 5/2010 Sykes

FOREIGN PATENT DOCUMENTS

| GB | 2174241 | 10/1986 |
| --- | --- | --- |
| JP | 04349644 | 5/2001 |
| JP | 2003130772 A | 5/2003 |
| JP | 2004125620 A | 4/2004 |
| WO | 2004083831 | 9/2004 |
| WO | 2006016136 A2 | 2/2006 |

OTHER PUBLICATIONS

USPTO, Office Action issued in related U.S. Appl. No. 12/161,055 dated Aug. 5, 2010.

Japanese Patent Office, Office Action issued in related Japanese Patent Application No. 2007-525342 dated Jun. 13, 2011 (partial translation provided).

* cited by examiner

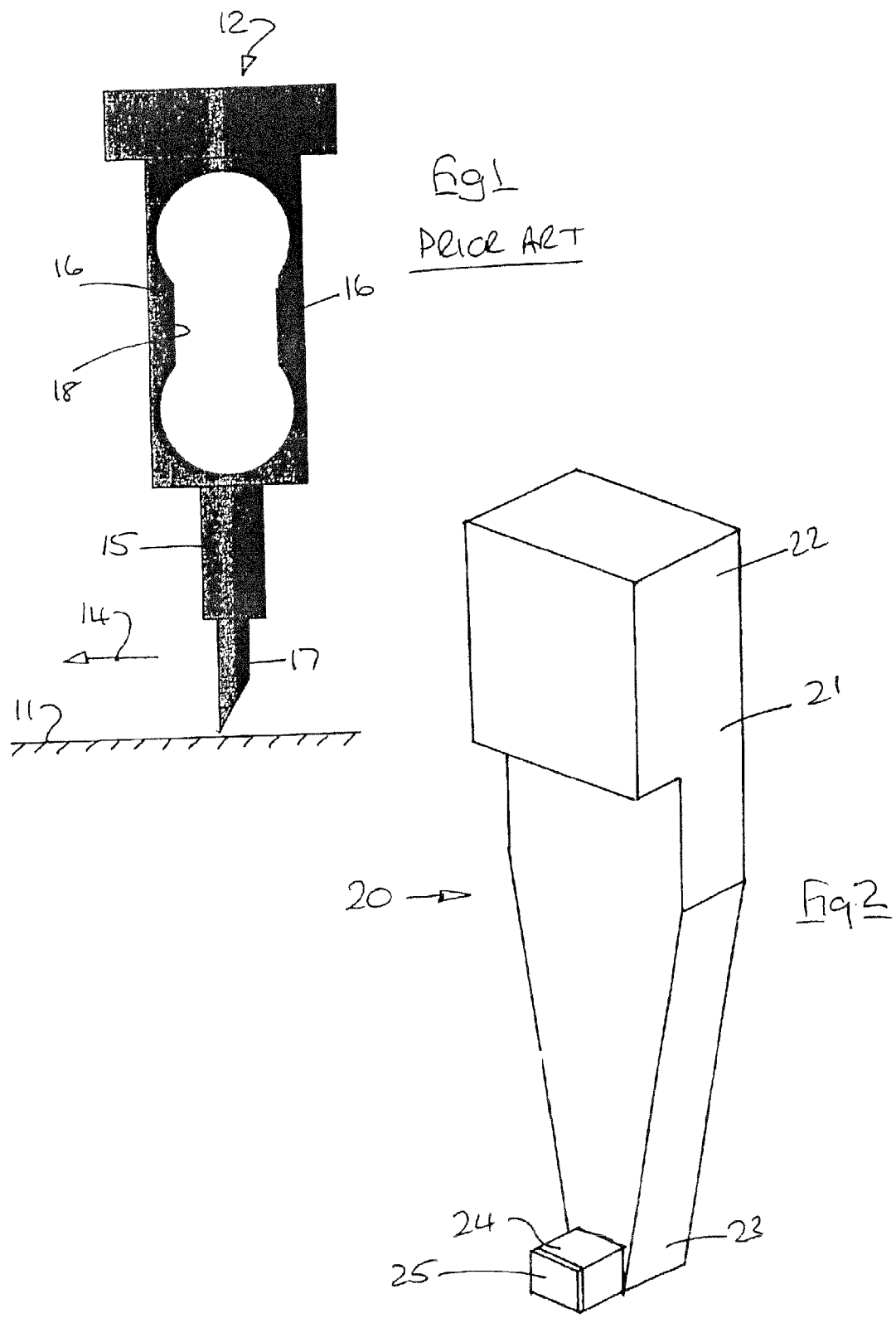

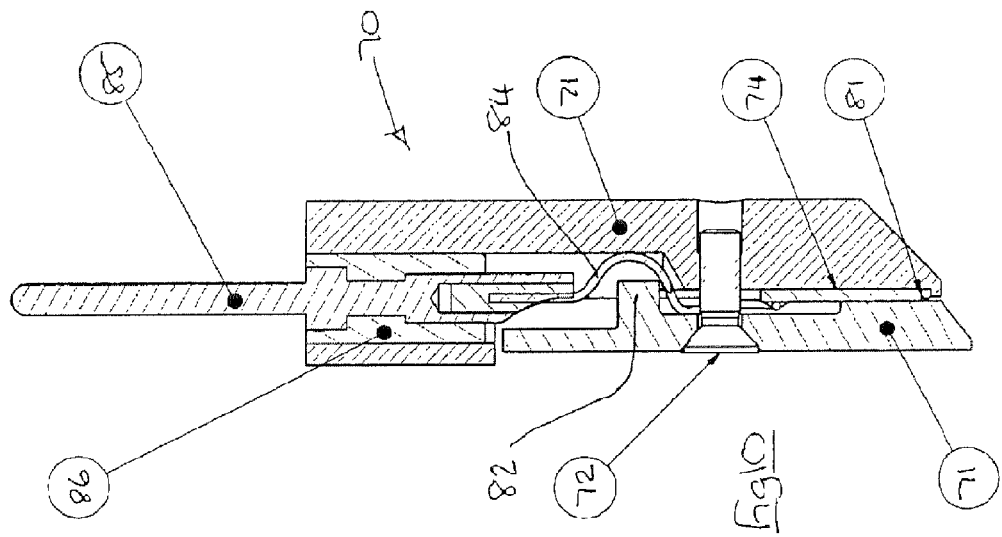
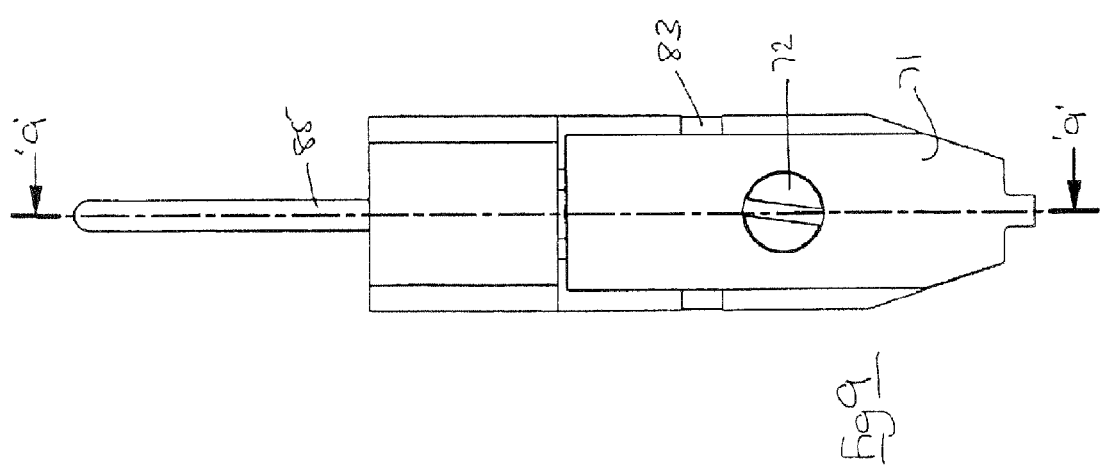

SHEAR TEST DEVICE

CROSS-REFERENCE TO RELATED APPLICATIONS

This application is a continuation of application Ser. No. 11/573,005, filed Sep. 11, 2008, which is the National Stage of International Application No. PCT/GB2005/003105, filed Aug. 5, 2005, which claims priority to Great Britain Application No. 0417773.9, filed Aug. 10, 2004 and Great Britain Application No. 0513896.1, filed Jul. 6, 2005. The content of each of these applications is hereby incorporated by reference herein in its entirety.

BACKGROUND

This invention concerns a device for testing the shear strength of a bond in a semiconductor device, and more particularly the strength of a bond between a substrate and a means of electrical connection thereto, typically a part-spherical deposit of solder or gold.

Semiconductor devices are very small, typically from 0.2 mm square to 25 mm square. These devices have sites for the bonding of electrical conductors thereto. Sites typically comprise part spherical deposits of gold or solder, collectively known as balls, which in use have the appearance of a squashed sphere or low circular dome, and a diameter in the range 50-1000 μm. These deposits form part of the electrical path between, for example, a printed circuit board and a chip, and may directly connect components, or may be joined to a conductor which is itself connected to another component. Many such balls may be provided as a regular grid-like array on a substrate.

Discrete balls are typically applied to a substrate and reflowed during subsequent connection to another component.

It is necessary to test the mechanical strength of the bond between the gold or solder deposit and the substrate in order to give confidence that the bonding method is adequate, and that the bond strength is sufficient. Difficulties arise because of the very small dimensions of the components, the precision with which the testing device must be positioned, and the very small forces and deflections which are to be measured.

It has been proposed to test the shear strength of such deposits by applying a tool to one side thereof. In order to avoid friction caused by the tool rubbing on the surface of the substrate, it is necessary for the tool to be just above the substrate surface. The height of the tool above the substrate must be closely controlled, typically within ±0.001 mm, to give accurate force measurement.

A known shear test apparatus comprises a machine having a support surface and a test head movable in a controlled manner relative to the support surface. The test head carries a cartridge specific to the test to be performed and having one of several interchangeable tools thereon. Typically the tool will be sized and/or shaped to suit the ball deposit to be tested. In use the substrate to be tested is attached to the support surface, and the tool is driven relatively against the ball deposit to perform the required test, which may be for example a shear test or a reciprocating fatigue test.

It will be understood that a typical tool is very small, and accordingly the cartridge has a flexible element on which is mounted one or more force gauges (such as strain gauges). Thus shear force between the tool and ball deposit is measured at a distance by deflection in the cartridge.

In the case of impact testing, where the tool is moving at high velocity before contact with the ball deposit, shear forces are not easy to detect. This is because the strain gauged element is somewhat remote from the tool, and the inertia of the cartridge masks the forces being measured. Typically the speed of the test is sufficiently high that the test is over before the strain gauge has time to respond to the forces at the tool.

BRIEF SUMMARY

According to a first aspect of the invention there is provided a test apparatus for applying shear loads to a ball deposit of gold or solder on a substrate, the apparatus comprising a support element, and a piezo-electric crystal on the support element, the support element being adapted to apply a shear load to a ball deposit via said crystal, thus placing the crystal under stress and causing an electrical signal to emanate therefrom.

Preferably the apparatus further includes a shield for the crystal, so that shear load is applied to the ball deposit via the shield.

The shield may comprise a protective surface applied directly to the crystal, or may be a tool element mounted on the support element and adapted to bear against the crystal. Such a tool element may be arranged to pre-load the crystal so as to improve stability thereof.

The shield may be adapted to the shape of the ball deposit to be tested, for example by having a part spherical recess adapted to engage a portion of the circumference of the ball deposit.

In a preferred embodiment the interface between the support element and the crystal, and/or between the crystal and the shield comprises a force distributing layer which is adapted to give substantially uniform planar contact. Such a layer may for example comprise an epoxy resin which is spread whilst fluid onto the respective interface surfaces, and cures after assembly of the apparatus to ensure that planar contact occurs. In this way point and line loads can be avoided.

The layer need only be very thin, and sufficient only to accommodate any misalignment which may be present. A particular advantage of epoxy resin is that the adjacent components are also retained in one another adhesively, so that the apparatus becomes unitary.

The layer may also provide an electrical insulator for the crystal or, depending on the electrical pathways, may be electrically conductive.

According to a second aspect of the invention there is provided a device for calibrating an apparatus adapted to apply shear loads to a ball deposit of gold or solder on a substrate, the device comprising a plate element having a flat surface and a through aperture at right angles to said surface, said aperture being sized to receive a wire of gold or solder whereby the wire is indexed to protrude above said surface, and said device is adapted to apply a shear load thereto.

A wire of gold or solder can very closely relate to the respective ball deposit, and hence give accurate calibration of one shear tool apparatus with respect to another. The device may include means for indexing a wire through said aperture on demand, and for determining the protrusion of wire above said surface per indexation. The means for indexing may be motor driven.

According to the second aspect, there is also provided a method of calibrating a shear tool for ball deposits of gold or solder, the method comprising the steps of: providing a flat surface with a through aperture at right angles thereto, providing a wire of gold or solder in said aperture, indexing said wire to protrude above said surface, and conducting a shear test with said tool against the protruding portion of said wire.

Wire is a consistent material, and well suited to repeat testing since the shear forces detected are closely repeatable. Accordingly successive shear tests using different shear tools can be correlated, and the shear sensors of the respective tools can be calibrated against a consistent standard.

The mechanical properties of wires are usually well known, and accordingly the shear forces detected using the method can be related to absolute as well as relative values.

BRIEF DESCRIPTION OF THE SEVERAL VIEWS OF THE DRAWINGS

Other features of the invention will be apparent from the following description of several preferred embodiments shown by way of example in the accompanying drawings, in which:

FIG. 1 schematically illustrates a prior test device;

FIG. 2 schematically illustrates on an enlarged scale, a test device according to the invention;

FIG. 9 shows a tool in front elevation;

FIG. 10 is a transverse section of the tool of FIG. 9 on line '9'-'9'; and

DETAILED DESCRIPTION

Figure 3:
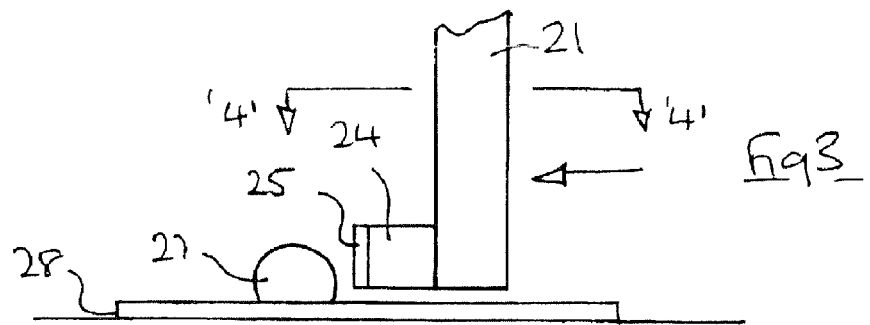
FIG. 3 illustrates a typical shear test in side elevation.

With reference to the drawings, FIG. 1 shows a prior test apparatus comprising a support surface 11, and a test head 12 movable relative thereto horizontally (XY) and vertically (Z). The test head comprises a cartridge to which a tool mounting 15 is attached by parallel arms 16. A test tool 17 is provided on the tool mounting 15.

In use, the tool is moved sideways in the direction of arrow 14 against a ball deposit mounted on the surface 11 to conduct a shear test, and the force is determined by strain gauges responsive to deflection of the arms 16. The tip of the test tool 17 is typically very small, and of the order of the diameter of the ball deposit, i.e., in the range 50-1000 µm.

FIG. 2 shows a first embodiment of the invention, and illustrates a tool 20 comprising a support element 21, the upper end 22 of which is adapted for direct connection to a prior art test head 12, or to a cartridge thereof in any suitable manner. The latter arrangement ensures interchangeability of components for existing test apparatus.

The lower end 23 tapers and has a piezo-electric crystal 24 attached thereto. The outer face of the crystal has a shield 25. The crystal is illustrated as a cube, but other shapes are of course possible, such as a cylinder.

The crystal has a width generally of the same order as the ball deposit to be tested, for example 100 µm. Not illustrated are the usual electrical connections of the crystal whereby changing stress of the crystal can be detected, and by calibration, calculation of the actual load.

The shield can be any suitable material covering adapted to protect the crystal from mechanical damage yet allow loads to be fully transmitted thereto. For example the shield may comprise a thin metal plate bonded to the crystal.

FIG. 3 illustrates the device of FIG. 2 in use and about to apply a shear load in the direction of arrow 26 against a ball deposit 27 mounted on a substrate 28.

Figure 4:
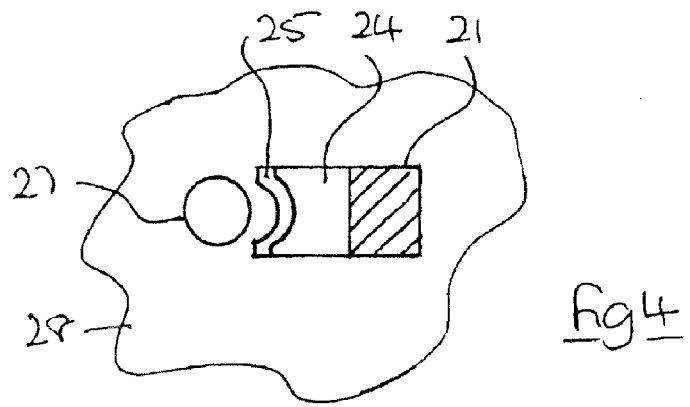
FIG. 4 is a view on line 4-4 of FIG. 3.

The sectional view of FIG. 4 shows how the shield and crystal may be adapted to the curved shape of the ball deposit 27.

Figure 5:
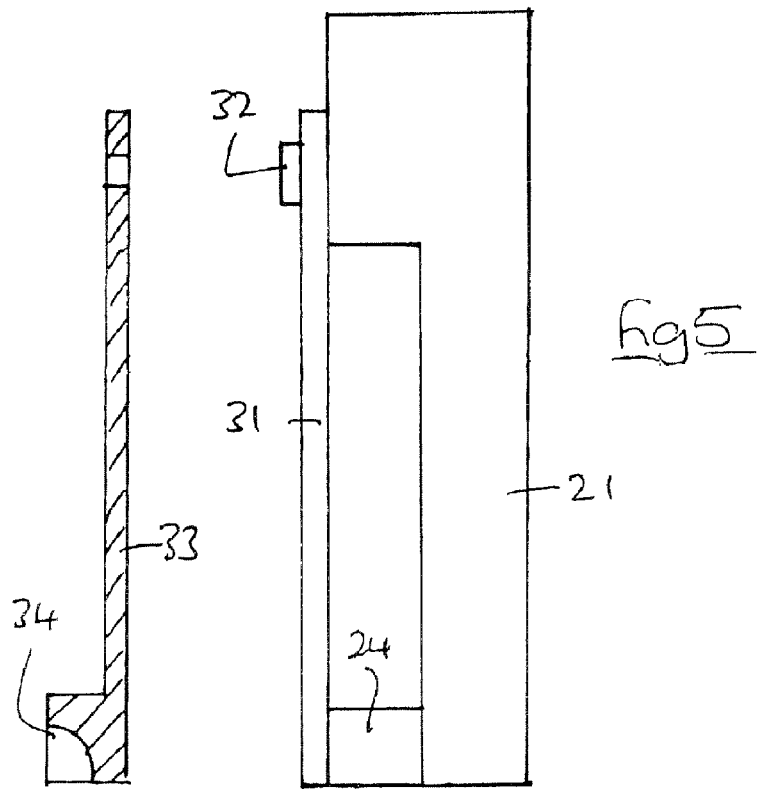
FIG. 5 is an alternative tool in side elevation, with a tool element shovel in longitudinal section.

A second embodiment is illustrated in FIG. 5 and comprises the support element 21 from which an anvil 31 is suspended on a pin 32 or clip of any suitable kind. The tool is plate-like and can directly apply a compressive load to the crystal 24. In a preferred embodiment the tool is biased against the crystal by internal resilience thereof, for example by reducing the thickness of the portion in contact with the upper end 22.

An alternative anvil 33 is illustrated in section, and has a part spherical recess 34 to closely engage the ball deposit.

Figure 6:
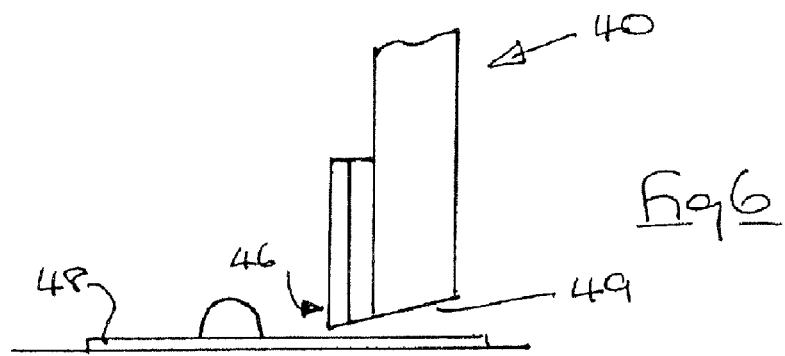
FIGS. 6-8 show alternative tools inside elevation.

FIG. 6 illustrates an alternative embodiment in which the undersurface of a tool 40 has an upward rake 49 so that the height of the leading edge 46 above the substrate 48 can be accurately determined prior to shear test. The rake may be any suitable angle (typically in the range 15-30°) which ensures clearance behind the leading edge whilst maintaining mechanical integrity of the tool.

Figure 7:
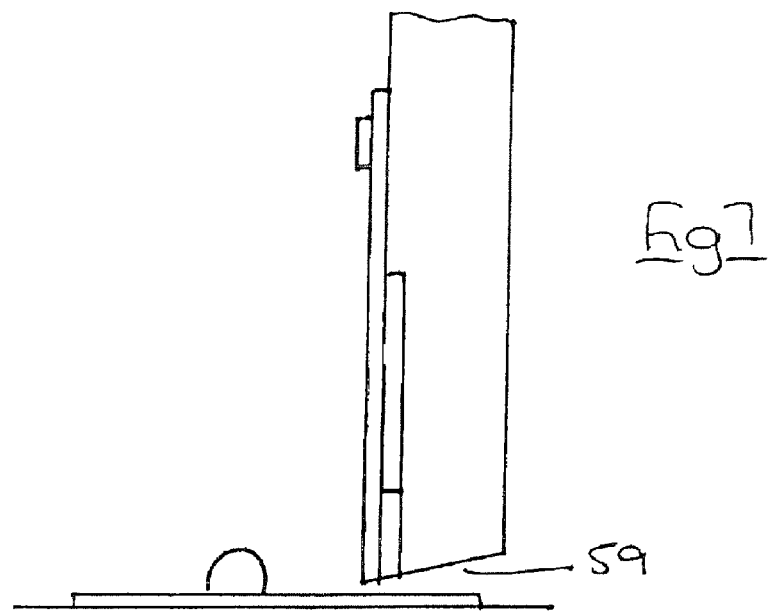
Figure 8:
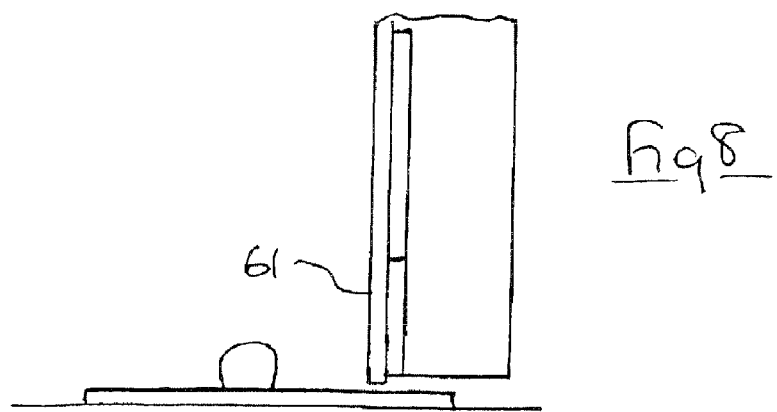

FIG. 7 corresponds to FIG. 5, and shows a similar negative rake 59. FIG. 8 shows an alternative anvil 61 which projects downwardly, as illustrated, so that a negative rake to the remainder of the tool is not required.

FIGS. 8 and 9 show an example arrangement of component parts of a typical tool 70.

A tool body 71, of e.g., brass, has a piezo-electric crystal 74 mounted thereon. As illustrated the crystal is partially recessed, and the sidewalls thereof are electrically insulated by a filament 81 of e.g. nylon.

A tool 71 is mounted to the front face of the body 71 by a countersunk screw 72; the countersink ensures correct positioning of the tool, and rotation is avoided by means of a peg 82 guided in a slot 83 of the body 71.

One face (the rear side) of the crystal 74 makes electrical contact with the body 71, whereas the front face has a lead 84 soldered thereto and connected through the interior of the body to a protruding contact 85. A suitable potting material 86 insulates the contact pin 85 from the body 71.

The piezo-electric crystal is a commercially available product, having approximate dimensions of 4 mm×2 mm, and a thickness of 0.3 mm. The material of the crystal is typically a tough, hard non-conductive ceramic such as zirconia.

The anvil 71 has a downward projection 87 for contact with a test deposit.

In all embodiments the interface between the crystal and body, and between the anvil and crystal, may comprise a load distributing layer of e.g. epoxy resin. The resin is spread whilst fluid, and cures to provide a load path which is assuredly planar. Slight imperfections in manufacture or assembly are thereby avoided, and as a consequence point and line transfer of loads is obviated. When cured, an epoxy resin has the advantage of holding the components in a unitary assembly, In use the tool is mounted in a test head, is lowered against the substrate, and withdrawn by a specified distance, using known techniques. The tool is then driven against the deposit to be tested, and shearing loads are transmitted directly from the anvil 71 to the piezo crystal 74, where strain deformation causes an electrical signal representative of load to be passed to suitable recording and analysing equipment; which need not be further described here.

One problem with tools which sense forces using elements such as strain gauges and piezo-electric crystals, is to calibrate the tools. Often it is not possible to determine absolute values (such as breaking loads measured in grams), and the user must rely on relative values which allow comparison of results. This latter technique is acceptable where only one test tool is being used, but becomes problematic when the test tool requires to be substituted, or results from several similar tools must be compared.

Figure 11:
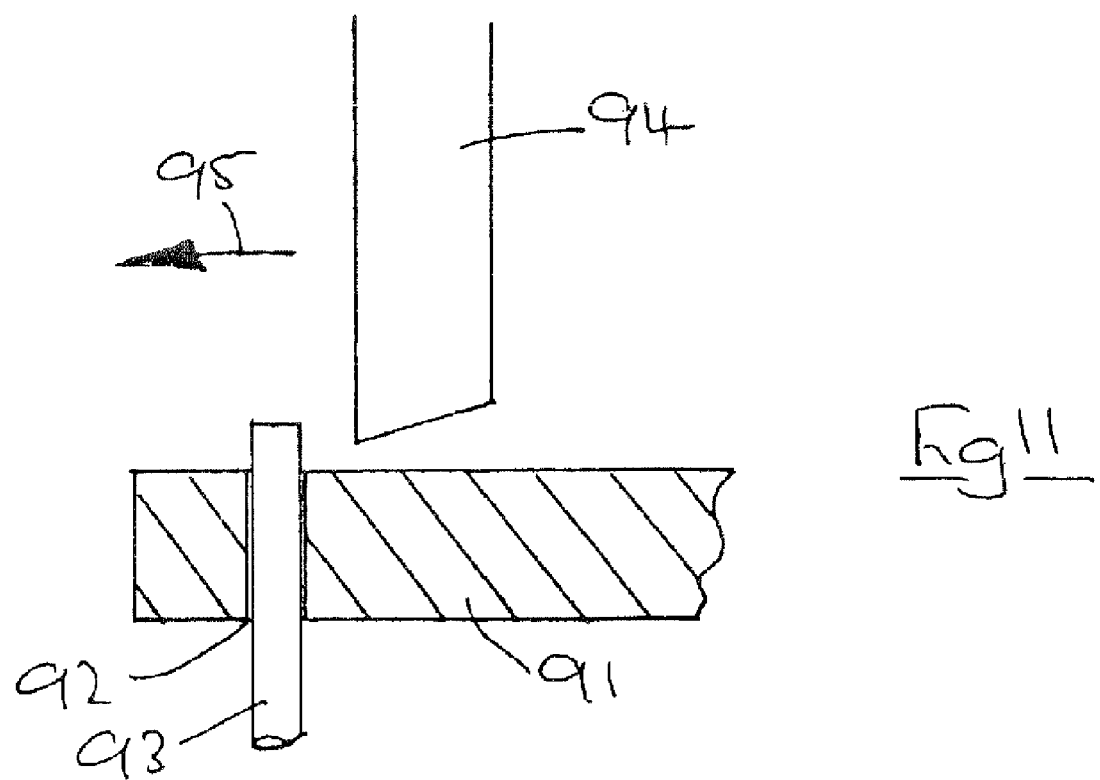
FIG. 11 illustrates a technique whereby the load/output of similar shear tools may be compared.

FIG. 11 illustrates a technique whereby the load/output of similar shear tools may be compared, and offers the possibility of also calibrating tools to give an absolute reading of breaking load.

A substrate 91 has an aperture 92 extending therethrough at right angles, and through which protrudes a wire 93. A test tool 94 driven in the direction of arrow 95 will shear the wire, and if suitably adapted can measure a relative breaking load. For example the tool may rely on electrical strain gauge or the piezo-electric crystal device described in this document.

The test may be repeated by indexing a further length of wire through the aperture. It will be appreciated that the length of wire above the aperture may not be critical, and that the test tool strikes the wire along the same axis at each test; these features make the test very simple to implement.

Wire is a very consistent material, and moreover is readily available as the precursor to the solder and gold balls which are applied to substrates used in semiconductor devices. Accordingly calibration tests can be effected using the precise materials to be tested in commercial use of test tool.

The aperture 92 should preferably be close fitting to the wire 93 to ensure that the test tool strikes at right angles.

It has been established that a shear test according to this method gives results which have excellent repeatability. Any likely effect of variable wire protrusion can be easily checked by empirical tests, and if consistent equal wire feed is necessary, a suitable indexing device may be incorporated.

The technique thus permits similar tools, and nominally identical tools to be calibrated so that results from several different tools can be compared. The technique is of particular value in the case of calibration of production test tooling which may be used in many different manufacturing locations.

It will also be appreciated that, using known information concerning the strength and material of the wire, it is possible to obtain a much better indication of absolute breaking loads, so that the technique allows test tools to be calibrated to give a read-out in e.g., grams, newtons or any other suitable unit.

What is claimed is:

1. A method of performing a shear test using a test tool, the method comprising:
   providing a surface with an aperture formed in the surface;
   indexing a wire through the aperture to protrude past the surface;
   contacting the portion of a wire protruding past the surface with the test tool to shear the portion of the wire off the remainder of the wire;
   measuring the shear load applied to the test tool by the portion of the wire while the portion of the wire is being sheared off by the test tool; and
   comparing the measured shear force with a shear force measured by a different test tool which was brought into contact with another portion of the wire.

2. The method of claim 1 wherein the aperture intersects the flat surface at a right angle.

3. The method of claim 1 further comprising:
   after measuring the shear force applied to the test tool by the portion of the wire, contacting a ball deposit bonded to a substrate with the test tool.

4. The method of claim 1 further comprising:
   measuring a length of the portion of the wire relative to the surface.

5. The method of claim 1 further comprising:
   moving the test tool to contact a ball deposit of gold or solder on a substrate of a type used in semiconductor devices.

* * * * *